(12) United States Patent
Swanson et al.

(10) Patent No.: US 10,492,007 B2
(45) Date of Patent: Nov. 26, 2019

(54) IMPULSE-AWARE SOUND PROCESSING

(71) Applicant: Cochlear Limited, Macquarie University, NSW (AU)

(72) Inventors: Brett Anthony Swanson, St. Ives (AU); Stefan J. Mauger, Macleod (AU); Phyu Phyu Khing, North Sydney (AU)

(73) Assignee: Cochlear Limited, Macquarie University (AU)

( * ) Notice: Subject to any disclaimer, the term of this patent is extended or adjusted under 35 U.S.C. 154(b) by 170 days.

(21) Appl. No.: 15/628,747

(22) Filed: Jun. 21, 2017

(65) Prior Publication Data

US 2018/0376257 A1 Dec. 27, 2018

(51) Int. Cl.
*H04R 25/00* (2006.01)
*G10L 21/0208* (2013.01)
*H04R 3/04* (2006.01)
*A61N 1/36* (2006.01)
*G10L 21/0364* (2013.01)
*G10L 21/06* (2013.01)

(52) U.S. Cl.
CPC ....... *H04R 25/505* (2013.01); *A61N 1/36038* (2017.08); *G10L 21/0208* (2013.01); *G10L 21/0364* (2013.01); *H04R 3/04* (2013.01); *H04R 25/48* (2013.01); *G10K 2210/1081* (2013.01); *G10K 2210/3028* (2013.01); *G10L 2021/065* (2013.01); *H04R 2225/67* (2013.01)

(58) Field of Classification Search
CPC .... G10K 2210/3028; G10K 2210/1081; G10L 2021/065; G10L 21/0208; H04R 3/04; H04R 25/48; H04R 25/505
See application file for complete search history.

(56) References Cited

U.S. PATENT DOCUMENTS

| | | | |
|---|---|---|---|
| 8,175,307 B2 | 5/2012 | Fischer | |
| 8,929,574 B2 | 1/2015 | Nielsen et al. | |
| 9,126,041 B2 | 9/2015 | Frühauf et al. | |
| 2014/0364681 A1* | 12/2014 | Hillbratt | H04R 25/30 600/25 |
| 2015/0163604 A1 | 6/2015 | Frühauf et al. | |
| 2017/0188160 A1* | 6/2017 | Pedersen | H04R 25/356 |

\* cited by examiner

*Primary Examiner* — Brian Ensey
(74) *Attorney, Agent, or Firm* — Edell, Shapiro & Finnan, LLC

(57) ABSTRACT

Techniques for addressing impulse sounds in an auditory prosthesis. The auditory prosthesis comprises a sound processor that is configured to convert received sound signals into output signals for use in generating stimulation for delivery to a recipient of the auditory prosthesis. The sound processor comprises an impulse-aware gain system that is configured to generate a time-variable gain for the application to the audio signal. The time-variable gain applied to the audio signal is dependent on both a level of the audio signal and the presence or absence of impulse sounds in the audio signal.

24 Claims, 12 Drawing Sheets

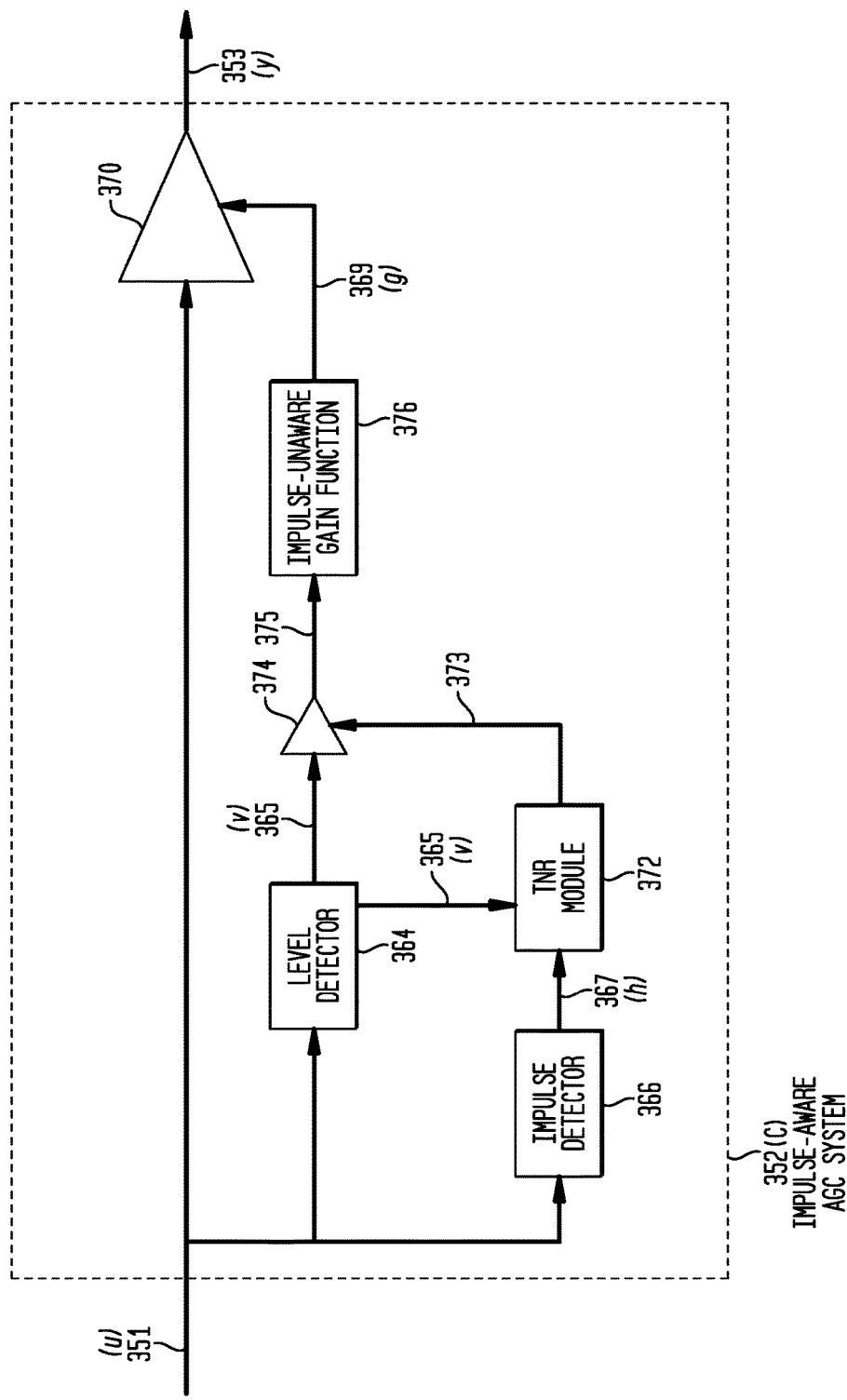

IMPULSE-AWARE SOUND PROCESSING

BACKGROUND

Field of the Invention

The present invention relates generally to auditory prostheses.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

Certain individuals suffer from only partial sensorineural hearing loss and, as such, retain at least some residual hearing. These individuals may be candidates for electro-acoustic hearing prostheses.

SUMMARY

In one aspect, a method is provided. The method comprises: receiving an audio signal at a sound input of an auditory prosthesis; detecting the presence of an impulse sound in a portion of the audio signal; generating, by one or more gain systems, a time-variable gain for application to the portion of the audio signal that includes the impulse sound, wherein the time-variable gain is decoupled from a level of the impulse sound; and applying, at a gain application module, the time-variable gain to the portion of the audio signal that includes the impulse sound to generate a compressed audio signal.

In another aspect, an auditory prosthesis is provided. The auditory prosthesis comprises: one or more sound input elements configured to receive an audio signal; and a sound processor configured to convert the audio signal into one or more output signals for use in delivering electrical stimulation to a recipient, wherein the sound processor comprises at least one impulse-aware gain system configured to detect an impulse sound within the audio signal and to apply a time-variable gain to the audio signal, where the time-variable gain is decoupled from energy that is part of the impulse sound.

In another aspect, an auditory prosthesis is provided. The auditory prosthesis comprises: at least one sound input element configured to receive an audio signal, and at least one gain system configured to attenuate the audio signal received at the at least one sound input element, wherein the attenuation that is applied to the audio signal is dependent on both a level of the audio signal and the presence or absence of impulse sounds in the audio signal.

BRIEF DESCRIPTION OF THE DRAWINGS

Embodiments of the present invention are described herein in conjunction with the accompanying drawings, in which:

FIG. 3C is a functional block diagram illustrating another arrangement for an impulse-aware gain system, in accordance with certain embodiments presented herein;

DETAILED DESCRIPTION

Auditory/hearing prosthesis recipients, such as cochlear implant recipients, are exposed to various types of noises on a daily basis. One particular type of noise is comprised of "impulse," "impulsive," or "transient" sounds. Impulse sounds are sounds that have a short overall duration (e.g., a duration on the order of a few milliseconds), are relatively loud (e.g., a level/amplitude that is well above the long-term sound average), and have a fast decay time (e.g., a decay time on the order of tens of milliseconds). Impulse sounds can originate from a large number of sources and may include, for example, firearm discharges, dishes clinking together, typing on a computer, keys rattling, doors slamming, chairs moving, hammering, etc. In many of these examples, the peak sound pressure level (SPL) of the impulse sounds are over 100 decibels (dB), and up to 180 dB. By some estimates, impulse sounds occur around one third of the time in everyday environments and could have a quality and performance decrease for certain auditory prosthesis recipients.

Presented herein are techniques for addressing impulse sounds in an auditory/hearing prosthesis. In accordance with certain embodiments presented herein, the auditory prosthesis comprises a sound processor that is configured to convert received sound signals into output signals for use in generating stimulation (e.g., electrical stimulation) for delivery to a recipient of the auditory prosthesis. The sound processor comprises an impulse-aware gain system that is configured to generate a time-variable gain (attenuation) for the application to the audio signal. The time-variable gain applied to the audio signal is dependent on both a level of the audio signal and the presence or absence of impulse sounds in the audio signal. The time-variable gain may be substantially decoupled from a level of the impulse sound and/or decoupled from energy that is part of the impulse sound (i.e., generated/derived substantially from energy that is not part of the impulse sound).

There are a number of different types of auditory/hearing prostheses in which embodiments of the present invention may be implemented. However, merely for ease of illustration, the techniques presented herein are primarily described with reference to one type of auditory prosthesis, namely a cochlear implant. However, it is to be appreciated that the techniques presented herein may be used in other auditory hearing prostheses, such as bone conduction devices, mechanical stimulators, auditory brainstem stimulators, electro-acoustic hearing prostheses, bimodal hearing prostheses, etc.

Figure 1A:
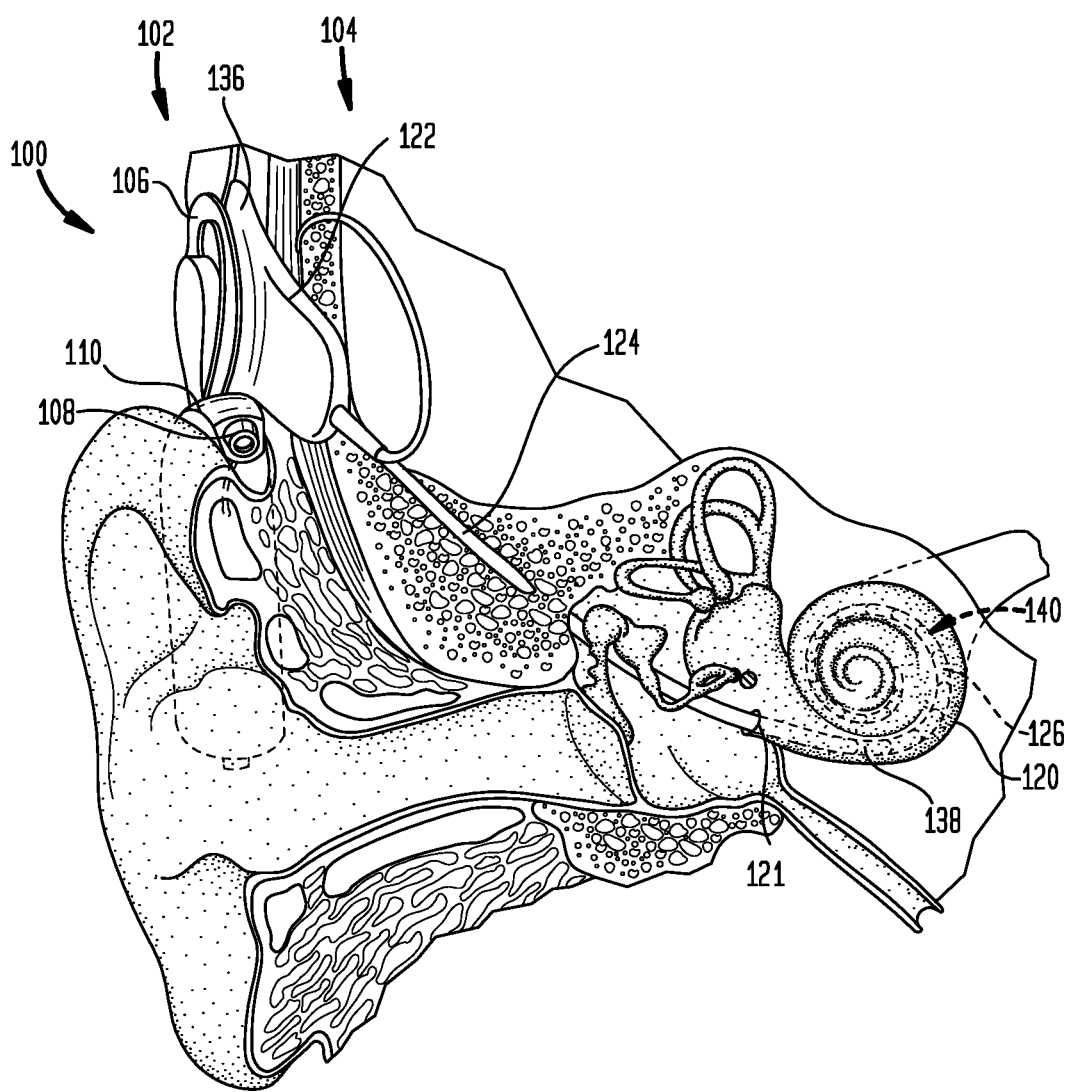
FIG. 1A is a schematic diagram of a cochlear implant in accordance with certain embodiments presented herein.
Figure 1B:
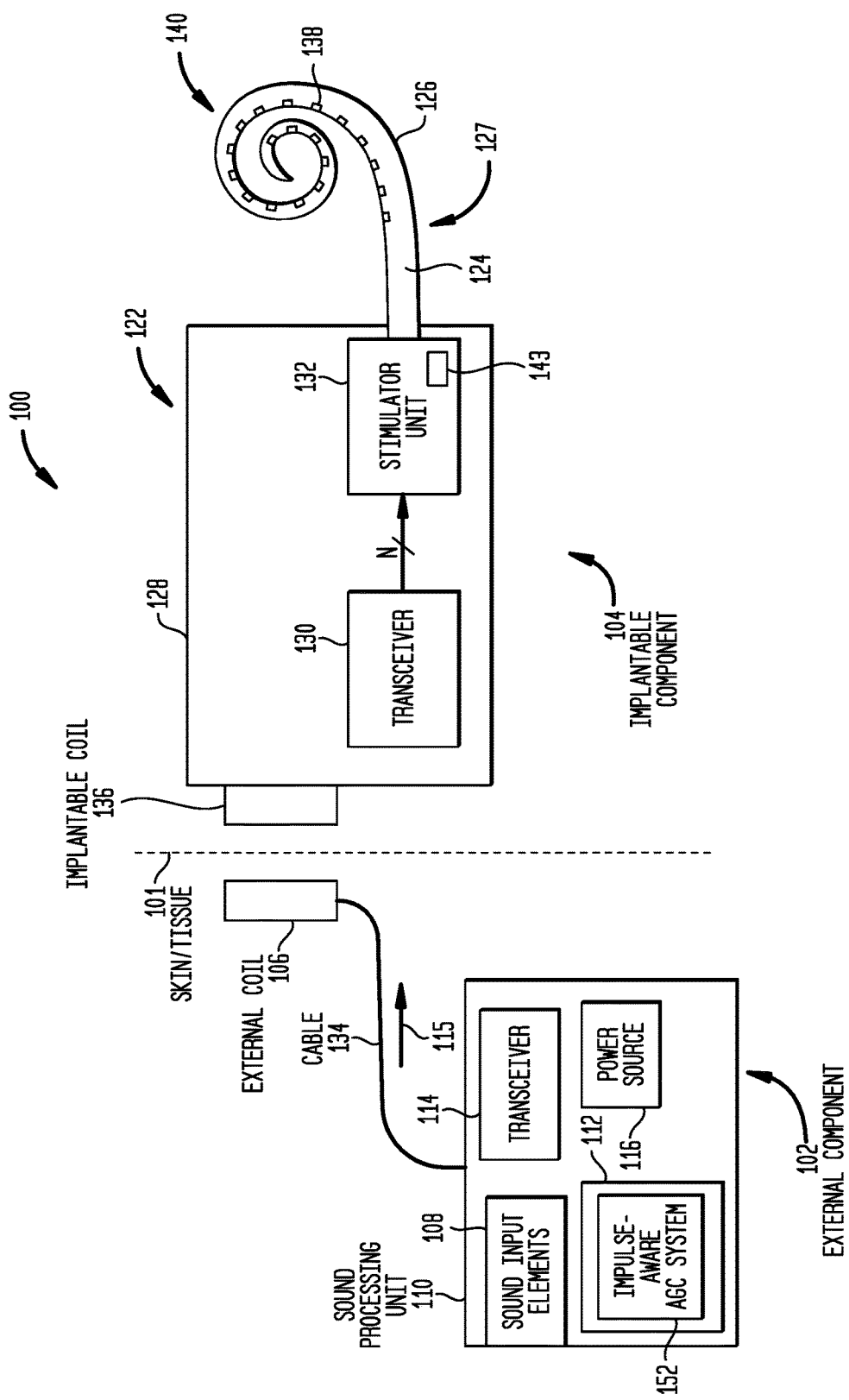
FIG. 1B is a block diagram of the cochlear implant of FIG. 1A.

FIG. 1A is a schematic diagram of an exemplary cochlear implant 100 configured to implement embodiments of the present invention, while FIG. 1B is a block diagram of the cochlear implant 100. For ease of description, FIGS. 1A and 1B will be described together.

The cochlear implant 100 comprises an external component 102 and an internal/implantable component 104 configured to be subcutaneously implanted within the recipient (i.e., under the skin/tissue of the recipient). The external component 102 comprises a sound processing unit 110, an external coil 106, and, generally, a magnet (not shown in FIGS. 1A and 1B) fixed relative to the external coil 106. The external coil 106 is connected to the sound processing unit 110 via a cable 134. The sound processing unit 110 comprises one or more sound input elements 108 (e.g., microphones, audio input ports, cable ports, telecoils, a wireless transceiver, etc.), a wireless transceiver 114, a sound processor 112, and a power source 116. The sound processing unit 110 may be, for example, a behind-the-ear (BTE) sound processing unit, an off-the-ear sound processor, or a body-worn sound processing unit, etc.

The implantable component 104 comprises an implant body (main module) 122, a lead region 124, and an elongate intra-cochlear stimulating assembly 126. The implant body 122 generally comprises a hermetically-sealed housing 128 in which an internal transceiver unit (transceiver) 130 and a stimulator unit 132 are disposed. The implant body 122 also includes an internal/implantable coil 136 that is generally external to the housing 128, but which is connected to the transceiver 130 via a hermetic feedthrough (not shown in FIGS. 1A and 1B). Implantable coil 136 is typically a wire antenna coil comprised of multiple turns of electrically insulated single-strand or multi-strand platinum or gold wire. The electrical insulation of implantable coil 136 is provided by a flexible molding (e.g., silicone molding), which is not shown in FIG. 1B. Generally, a magnet is fixed relative to the implantable coil 136.

Elongate stimulating assembly 126 is configured to be at least partially implanted in the recipient's cochlea 120 (FIG. 1A) and includes a plurality of longitudinally spaced intra-cochlear electrical stimulating contacts (electrodes) 138 that collectively form a contact or electrode array 140 for delivery of electrical stimulation (current) to the recipient's cochlea.

Stimulating assembly 126 extends through an opening 121 in the cochlea (e.g., cochleostomy, the round window, etc.) and has a proximal end connected to stimulator unit 132 via lead region 124 and a hermetic feedthrough (not shown in FIG. 1B). Lead region 124 includes a plurality of conductors (wires) that electrically couple the electrodes 138 to the stimulator unit 132.

Returning to external component 102, the sound input element(s) 108 are configured to detect/receive input sound signals and to generate electrical input signals therefrom. The sound processor 112 is configured to execute sound processing and coding to convert the electrical input signals received from the sound input elements into output signals that represent electric (current) stimulation for delivery to the recipient. That is, as noted, the cochlear implant 100 operates to evoke perception by the recipient of sound signals received by the sound input elements 108 through the delivery of electrical stimulation signals to the recipient. The output signals are represented in FIG. 1B by arrow 115.

The output signals 115 are, in the examples of FIGS. 1A and 1B, encoded data signals that are sent to the implantable component 104 via external coil 106. More specifically, the magnets fixed relative to the external coil 106 and the implantable coil 136 facilitate the operational alignment of the external coil 106 with the implantable coil 136. This operational alignment of the coils enables the external coil 106 to transmit the encoded data signals, as well as power signals received from power source 116, to the implantable coil 136. In certain examples, external coil 106 transmits the signals to implantable coil 136 via a radio frequency (RF) link. However, various other types of energy transfer, such as infrared (IR), electromagnetic, capacitive and inductive transfer, may be used to transfer the power and/or data from an external component to an implantable component and, as such, FIG. 1B illustrates only one example arrangement.

In general, the encoded data and power signals are received at the transceiver 130 and the data signals are provided to the stimulator unit 132. The stimulator unit 132 is configured to utilize the encoded data signals to generate electrical stimulation (e.g., current) for delivery to the recipient's cochlea via one or more of the electrodes 138. In this way, cochlear implant 100 electrically stimulates the recipient's auditory nerve cells, bypassing absent or defective hair cells that normally transduce acoustic vibrations into neural activity, in a manner that causes the recipient to perceive one or more components of the received sound signals.

In accordance with embodiments presented herein, the sound processor 112 comprises, among other elements, an impulse-aware gain system 152. As described further below, when impulse (transient) sounds are detected in sound signals received at the sound input element(s) 108, one or more operations of the impulse-aware gain system 152 are disabled/suspended so that the impulse sounds pass there through to a loudness growth function (LGF) with limited attenuation.

Figure 2:
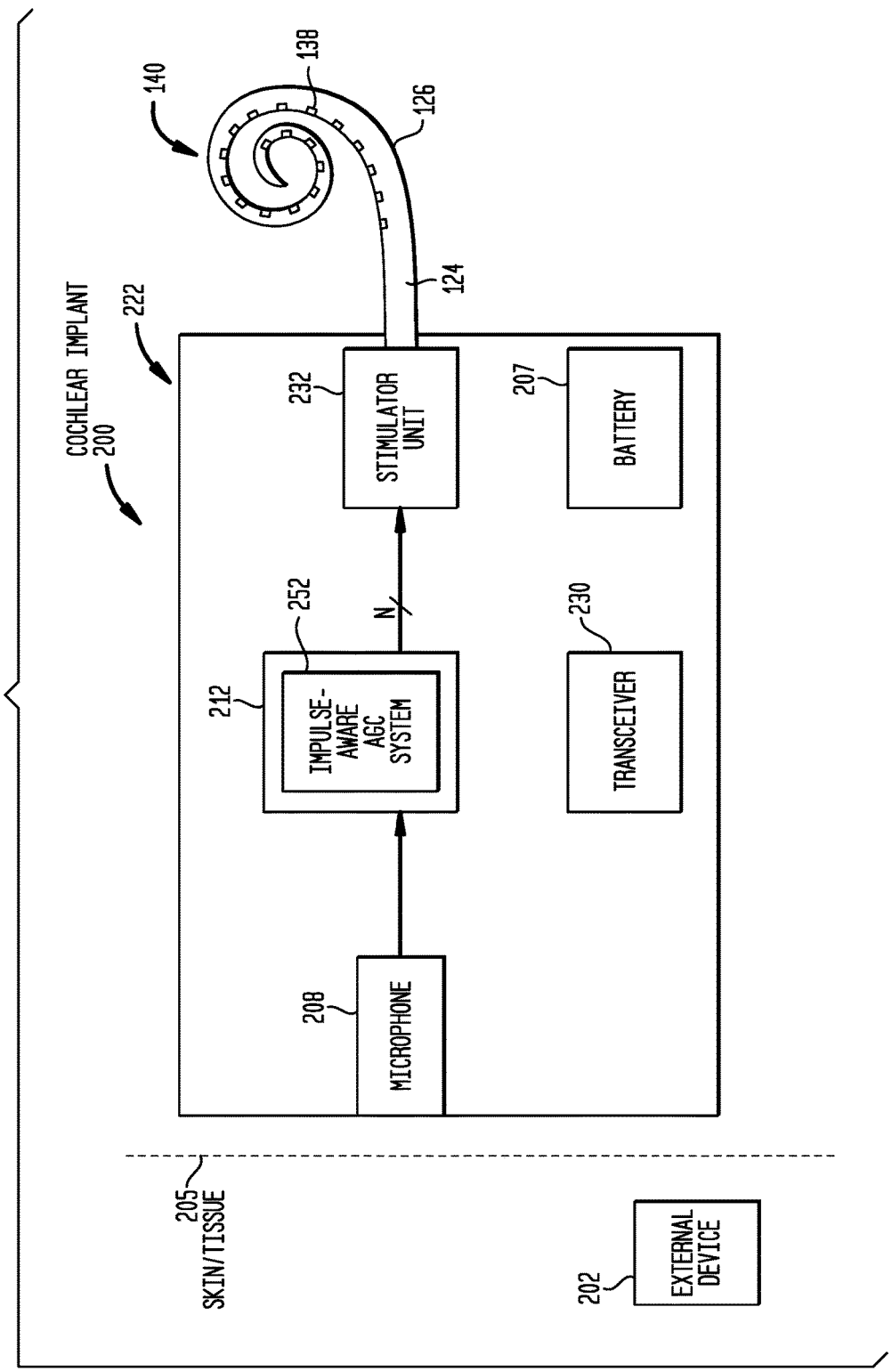
FIG. 2 is a block diagram of another cochlear implant in accordance with certain embodiments presented herein.

FIGS. 1A and 1B illustrates an arrangement in which the cochlear implant 100 includes an external component. However, it is to be appreciated that embodiments of the present invention may be implemented in cochlear implants having alternative arrangements. For example, FIG. 2 is a functional block diagram of an exemplary totally implantable cochlear implant 200 configured to implement embodiments of the present invention. Since the cochlear implant 200 is totally implantable, all components of cochlear implant 200 are configured to be implanted under skin/tissue 205 of a recipient. Because all components are implantable, cochlear implant 200 operates, for at least a finite period of time, without the need of an external device. An external device 202 can be used to, for example, charge the internal power source (battery) 207. External device 202 may be a dedicated charger or a conventional cochlear implant sound processor.

Cochlear implant 200 includes an implant body (main implantable component) 222, that includes one or more implantable sound sensors, such as an implantable microphone 208, an internal transceiver unit (transceiver 230), a sound processor 212, a stimulator unit 232, and the battery 207. The microphone 208 may be disposed in, or electrically connected to, the implant body 222. The cochlear implant also includes an elongate intra-cochlear stimulating assembly 126 as described above with reference to FIGS. 1A and 1B.

The transceiver unit 230 permits cochlear implant 200 to receive and/or transmit signals to external device 202. For example, transceiver unit 230 may be configured to transcutaneously receive power and/or data from external device 202. However, as used herein, transceiver unit 230 refers to any collection of one or more implanted components which form part of a transcutaneous energy transfer system. Further, transceiver unit 230 includes any number of component (s) which receive and/or transmit data or power, such as, for example a coil for a magnetic inductive arrangement, an antenna for an alternative RF system, capacitive plates, or any other suitable arrangement.

The sound processor 212 is configured to execute sound processing and coding to convert received/detected sound signals (e.g., received by microphone 208 and/or other sound sensors) into output signals representation stimulation (e.g., current levels) for delivery to a recipient. Similar to the sound processor 112 of FIGS. 1A and 1B, sound processor 212 comprises, among other elements, an impulse-aware gain system 252. As described further below, when impulse (transient) sounds are detected in sound signals received at the microphone 208, one or more operations of the impulse-aware gain system 252 are disabled/suspended so that the impulse sounds pass through with limited attenuation.

As noted above, FIG. 1A illustrates an embodiment in which the external component 102 includes the sound processor. As such, in the illustrative arrangement of FIG. 1A, output signals generated by the sound processor 112 are provided to the implanted stimulator unit 120 via the RF link between the external coil 106 and the internal coil 136. However, in the embodiment of FIG. 2, the sound processor 212 is implanted in the recipient. As such, the output signals generated by the sound processor 212 do not traverse the RF link, but instead are provided directly to the stimulator unit 232.

Figure 3A:
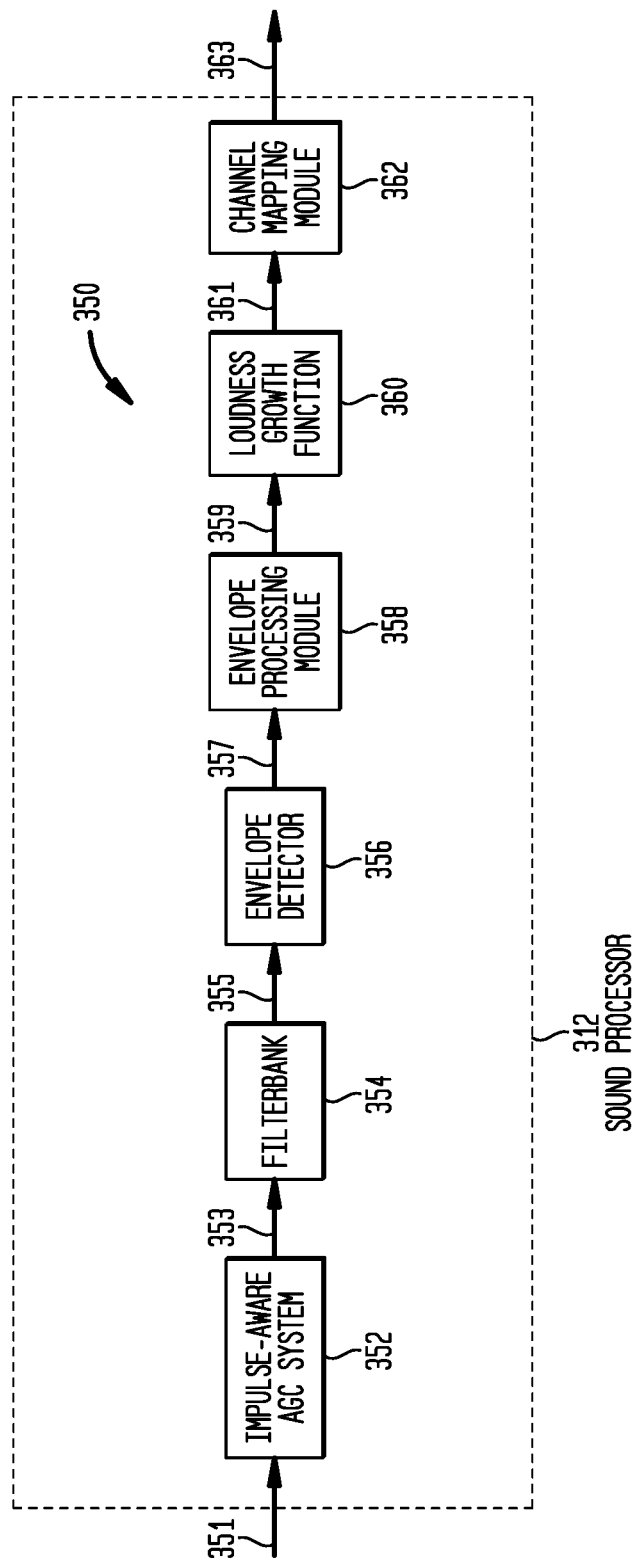
FIG. 3A is a functional block diagram illustrating a sound processing path of a sound processor, in accordance with certain embodiments presented herein.

As noted above, the cochlear implants 100 and 200 each include a sound processor (e.g., sound processors 112 and 212, respectively) configured to implement embodiments of the techniques presented herein. FIG. 3A is a block diagram illustrating one example embodiment of a sound processor, referred to as sound processor 312, in accordance with embodiments presented herein.

More specifically, FIG. 3A illustrates a sound processing path 350 for sound processor 312 that is configured to convert received audio/sound signals into output signals, sometimes referred to herein as stimulation control signals, that are useable by a stimulator unit to generate electrical stimulation (current) for delivery to a recipient. In the embodiment of FIG. 3A, the sound processing path 350 is implemented as part of a digital signal processor (DSP) and is formed by a plurality of functional modules that include an impulse-aware gain system 352, a filterbank module (filterbank) 354, an envelope detection module (envelope detector) 356, an envelope processing module 358, a Loudness Growth Function (LGF) 360, and a channel mapping module 362.

As shown, an audio signal 351 (e.g., from one or more microphones) is provided to the impulse-aware gain system 352. The audio signal 351 includes target/desired sounds (e.g., speech) and, as described further below, may also include undesired impulse (transient) sounds. In general, the impulse-aware gain system 352 is configured to apply a time-variable/time-varying gain (i.e., attenuation) to the audio signal 351 so as to produce a compressed audio signal 353. However, as described further below, the impulse-aware gain system 352 is configured to operate in a manner such that impulse sounds detected within the audio signal 351 receive minimal additional attenuation. That is, the attenuation applied to the impulse sound is decoupled from (i.e., generally/substantially unrelated to) the level of the impulse sound and may be decoupled from energy that is part of the impulse sound (i.e., the impulse sound is largely excluded from the attenuation determination process). Further details and operations of the impulse-aware gain system 352 are described below with reference to FIGS. 3B and 3C.

Figure 4:
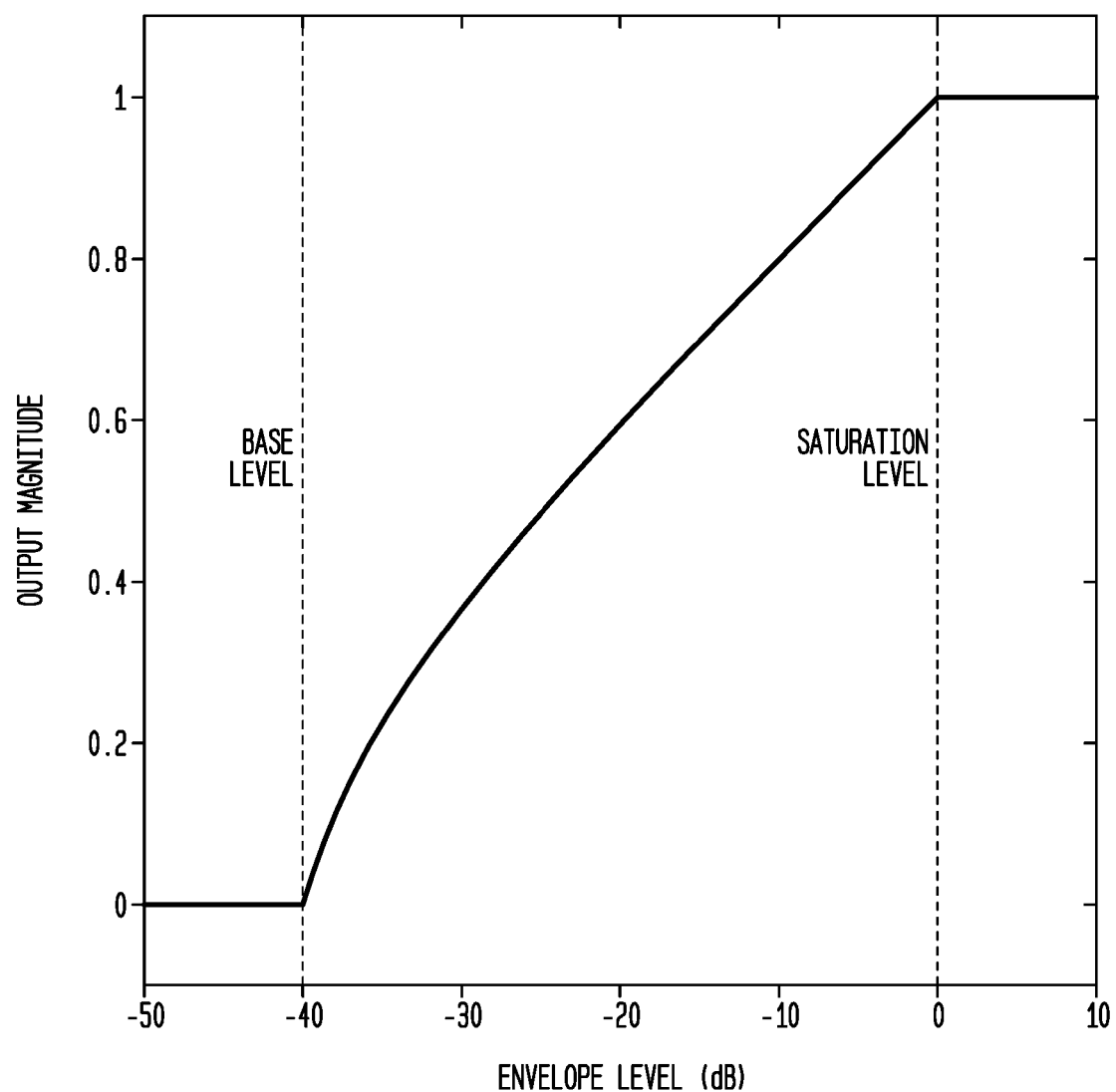
FIG. 4 is a graph illustrating the input-output function of a Loudness Growth Function (LGF) of a sound processor, in accordance with certain embodiments presented herein.

The compressed audio signal 353 is applied/provided to the filterbank 354, which is configured to produce multi-channel filter outputs 355. The filter outputs 355 are applied to the envelope detector 356, which is configured to produce channel envelopes 357. The channel envelopes 357 may optionally be further processed at envelope processing module 358 to produce processed channel envelopes 359. Examples of optional envelope processing operations include Adaptive dynamic range optimization (ADRO) and maxima selection. The processed channel envelopes 359 (or alternatively the channel envelopes 357) are applied to the LGF 360, which is configured to produce channel magnitude signals 361. The LGF 360 is an instantaneous non-linear compressive function, with an input-output function shown in FIG. 4. The shape of the LGF 360 is intended to make the cochlear implant recipient's loudness perception match that of a normal hearing person for changes in sound intensity. To avoid excessive loudness, the stimulation current is not allowed to exceed a comfortable/comfort level, sometimes referred to as the "C" level of a channel. The comfortable level is the level at which a stimuli that is perceived by the recipient as comfortably loud. The LGF 360 is configured such that a channel envelope greater than or equal to the saturation level produces a magnitude of 1.0. The saturation level of the LGF 360 is the envelope level of a channel that produces current at the comfortable level of the channel.

The channel magnitudes 361 generated by the LGF 360 are applied to the channel mapping module 362 to produce output signals (current levels) 363 for stimulation pulses that are to be delivered to the recipient so as to evoke perception of the audio signal 351. In certain embodiments, the channel mapping module 362 can calculate the current level of a stimulation pulse as:

current_level=lower_level+magnitude*(upper_level−lower_level), where the "lower_level" is the lowest allowed current level for the associated channel (sometimes referred to as the perceptual threshold level, threshold level, or "T-level" of the channel), and the "upper_level" is the highest allowed current level for the associated channel (i.e., the C-level of the channel). That is, a cochlear implant provides an electrical output, which is scaled between the T-level (i.e., a softest electrical stimuli that is perceivable by the recipient) and the C-level (i.e., a stimuli that is perceived by the recipient as comfortably loud). The electrical stimuli (including those produced by impulse sounds) do not exceed the C-level. A recipient can have different T-levels and different C-levels at different channels.

In summary, FIG. 3A illustrates that the sound processing path 350 is configured to convert audio signals into current levels that can used to stimulate a recipient to evoke perception of the sound signals. At each channel, the current levels are mapped between the recipient's threshold level and comfortable level. In FIG. 3A, the arrows 351 and 353 represent single-channel signals, while the arrows 355, 357, 359, 361, and 363 represent multi-channel signals where each "channel" is a frequency range that is associated with one or more electrodes implanted in the recipient.

As noted above, FIGS. 3B and 3C illustrate further details of two embodiments of the impulse-aware gain system 352 shown in FIG. 3A. For ease of illustration, the embodiment of the impulse-aware gain system 352 shown in FIG. 3B is referred to as impulse-aware gain system 352(B), while the embodiment of the impulse-aware gain system 352 shown in FIG. 3C is referred to as impulse-aware gain system 352(C).

Figure 3B:
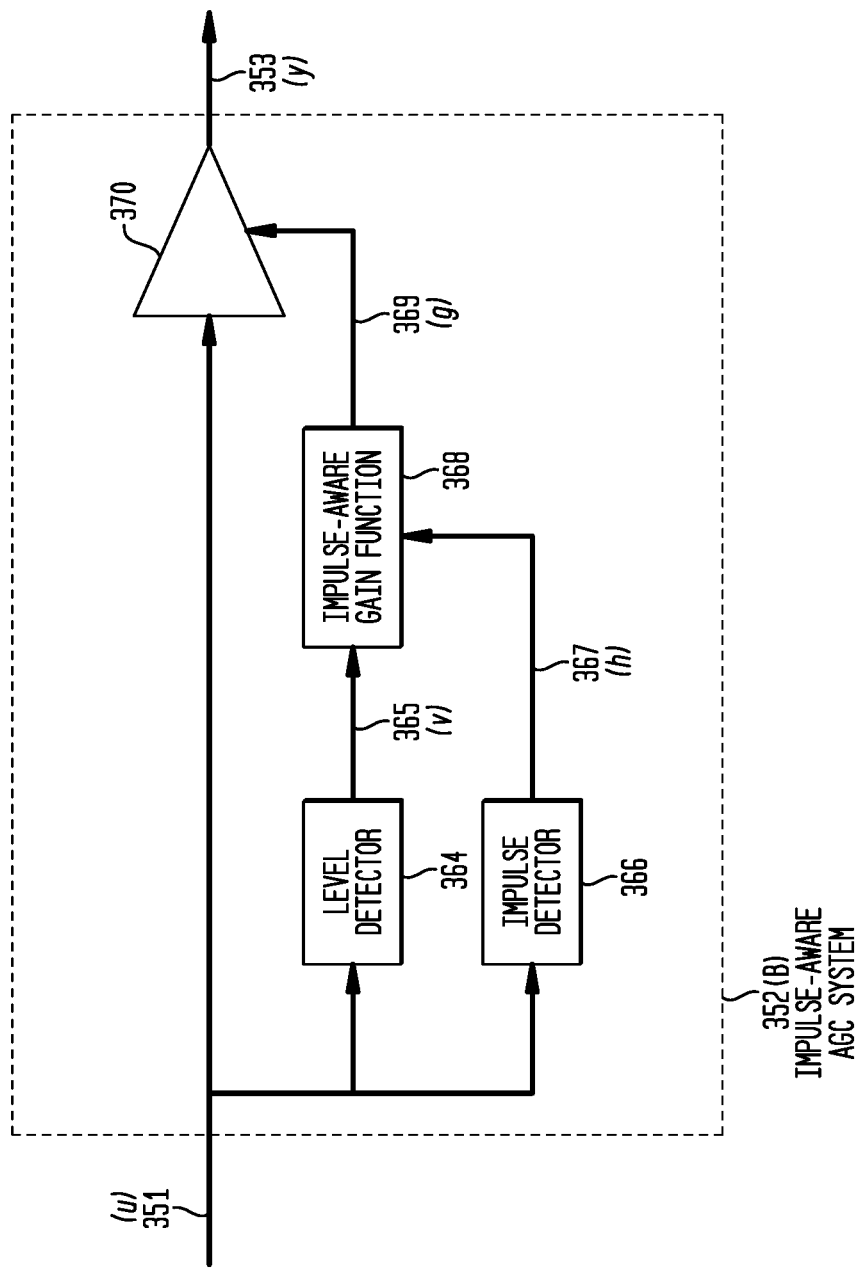
FIG. 3B is a functional block diagram illustrating one arrangement for an impulse-aware gain system, in accordance with certain embodiments presented herein.

Referring first to FIG. 3B, the impulse-aware gain system 352(B) comprises a level detector 364, an impulse detector 366, an impulse-aware gain function 368, and a gain application module 370. In operation, the audio signal 351 ($u$) is applied/provided to the level detector 364, which produces a level signal 365 ($v$). The level signal 365 is applied to the impulse-aware gain function 368 which, in certain circumstances, generates a time-variable gain 369 ($g$). The time-variable gain 369 generated by the impulse-aware gain function 368 is applied to the audio signal 351 at the gain application module 370. In general, the gain 369 operates to reduce (attenuate) the audio signal amplitude when the level signal 365 exceeds a threshold or kneepoint. As such, application of the time-variable gain 369 to the audio signal 351 produces the compressed audio signal 353 ($y$).

Returning briefly to FIG. 3A, the sound processing path 350 is typically calibrated so that sounds at a specified level (e.g., 65 dB SPL) result in processed channel envelopes 359 (or alternatively channel envelopes 357) just reaching the LGF 360 saturation level, thereby ensuring that the magnitudes 361 just reach a value of 1.0 and that stimulation current levels 363 just reach the comfortable level for the channel. If no gain system was present, then sounds at higher presentation levels would produce envelope levels exceeding the LGF saturation level and, as such, the resulting channel magnitudes would be clipped. Therefore, the general purpose of the impulse-aware gain system 352 is to manipulate (i.e., attenuate) the audio signals in order to avoid signal clipping, distortion, and other degradations and to present the wide dynamic range of sounds in the smaller dynamic range found in electric hearing.

Returning once again to FIG. 3B, in certain circumstances, the impulse-aware gain function 368 is an Automatic Gain Control (AGC) system that operates in accordance with one or more "attack times" and/or "release times" and can be triggered at an audio signal level, referred to as a "kneepoint." If the detected audio signal 351 has an amplitude (level) which crosses above the kneepoint, then the impulse-aware gain function 368 is activated to implement a reduction in the gain (i.e., the gain in dB is negative). The initial gain reduction typically occurs over a relatively short time period (the "attack time"). When the level reduces below the kneepoint, the gain gradually recovers back to its default value, typically over a longer time period (the "release time"). It is to be appreciated than a gain system in accordance with embodiments presented herein may also or alternatively include multiple stages that each having different associated kneepoints and release times.

It has been found that a Slow AGC (i.e., an AGC with a long release time, such as 625 milliseconds) provides better speech intelligibility for cochlear implant recipients than a Fast AGC (i.e., an AGC with a short release time, such as 75 milliseconds). However, with a Slow AGC, some recipients notice sound drop-outs following impulse sounds. As noted above, impulse sounds are sounds that have a short overall duration (e.g., a duration on the order of a few milliseconds), are relatively loud (e.g., a level/amplitude that is well above the long-term sound average), and have a fast decay time (e.g., a decay time on the order of tens of milliseconds). In a cochlear implant that includes an implantable microphone, impulse/impulsive sounds are prevalent due to body actions such as chewing, coughing, etc.

Conventional gain systems attempt to remove impulse sounds through attenuation of the audio signal (i.e., through application of large negative gains) wherein the attenuation is based entirely on the level of the audio signal (including any impulse sounds there within). For example, one prior art solution to impulse sounds is a dual-loop AGC, which is essentially a Slow AGC followed by a Fast AGC. The Fast AGC attempts to suppress impulse sounds by quickly applying a large negative gain that attenuates the audio signal. However, one problem with this solution is that it is difficult to find an optimum value for the release time. Some impulse sounds have such a short duration (e.g. 10 ms) that typical release times (e.g., 75 ms) will cause a speech or otherwise desired signal that immediately follows the impulse sound to be unnecessarily suppressed. A second problem occurs when the audio signal level changes suddenly from a low level (below the Slow AGC threshold) to a high level (above the Slow AGC threshold). The Slow AGC will take approximately a second to respond, and during this time the Fast AGC will act. As mentioned previously, it has been shown that a Fast AGC reduces speech intelligibility, thus the recipient may not be able to understand the high level speech for several seconds.

In accordance with the embodiments presented herein, the impulse-aware gain system 352(B) is configured to operate in a manner that is substantially opposite to conventional arrangements and, as such, does not suffer from the drawbacks prevalent in conventional arrangements. In particular, conventional gain functions exclusively use the audio signal level to control the activation/generation of a gain. In contrast, the impulse-aware gain system 352(B) is configured with an additional secondary input that controls the level of gain that is applied to the audio signal. That is, in the impulse-aware gain system 352(B) of FIG. 3B, the gain that is applied to the audio signal is dependent on both the audio signal level and the presence or absence of impulse sounds in the audio signal. Due to the use of this secondary control mechanism, the techniques presented herein allow the use of a Slow AGC without the problem of sound drop-outs following impulse sounds.

More specifically, as noted above and as shown in FIG. 3B, the impulse-aware gain system 352(B) includes the impulse detector 366. The impulse detector 366 is configured to analyze the audio signals 351 for the presence (or absence) of impulse (transient) sounds and produces an output signal 367, sometimes referred to herein as a Boolean or logic signal (h), which indicates the presence (or absence) of impulse sounds in the audio signals. The Boolean signal 367 is True when an impulse sound is present, and is False when no impulse sound is present. The Boolean signal 367 is applied to the impulse-aware gain function 368. The impulse-aware gain function 368 has two modes of operation that are activated based on the level of the Boolean signal 367 (i.e., based on the presence or absence of impulse sounds, as determined by the impulse detector 366).

First, when the Boolean signal 367 is False (i.e., zero or low), the impulse-aware gain function 368 operates in a first mode to generate a time-variable gain based on the level signal 365 is determined by the level detector 364. That is, in the first mode of operation, the impulse-aware gain function 368 operates as described above in accordance with one or more kneepoints and release times to attenuate the audio signal, as needed. Second, when the Boolean signal 367 is True (i.e., one or high), one or more operations of the impulse-aware gain function 368 are disabled/suspended so as to hold the gain 369 at its previous value (i.e., g is held at a constant level). That is, when an impulse sound is detected, the combination of the impulse detector 366 and the impulse-aware gain function 368 effectively prevent the gain from changing (i.e., from adapting and applying large negative gains to the signal) and the gain (i.e., the amount of attenuation) is based on a level of the audio signal prior to detection of the impulse sound. The gain is held constant for the duration of the impulse sound and the gain is based on a time period (i.e., a sample) obtained from before receipt of the impulse sound. By limiting attenuation from impulses, the target signal will remain louder.

In other words, the impulse-aware gain system 352(B) operates in an opposite manner to conventional arrangements in that the gain system deliberately does not suppress the impulse sound. Instead, the techniques presented herein allow the impulse sounds to pass through to the subsequent LGF 360 (FIG. 3A) to prevent the impulse sound from being too loud. Because the LGF 360 acts instantaneously (i.e., it has zero attack and release times), there is no detrimental effect on speech that immediately follows the impulse sound.

As noted, FIG. 3C illustrates another embodiment for the impulse-aware gain system 352, referred to as impulse-aware gain system 352(C). The impulse-aware gain system 352(C) comprises the level detector 364, the impulse detector 366, and the gain application module 370, which may all be implemented similarly to as described with reference to FIG. 3B. The impulse-aware gain system 352(C) also comprises a transient noise reduction (TNR) module 372, a secondary gain application module 374 (e.g., a TNR gain application module), and an impulse-unaware gain function 376.

The impulse-aware gain system 352(C) may generally be described as including a first processing path and a second processing path over which the audio signal 351 is forwarded in parallel. The first processing path corresponds to the directly delivery of the audio signal 351 to the gain application module 370. The second processing path is comprised of the TNR module 372, the secondary gain application module 374, and the impulse-unaware gain function 376. As descried further below, any impulse sounds within the audio signal are actively attenuated in the audio signal forwarded on the second processing path before the audio signal reaches the at least one gain function. However, these operations at the second processing path do not affect the audio signal in the first processing path.

More specifically, in the embodiment of FIG. 3C, the audio signal 351 ($u$) is applied/provided to the level detector 364, which produces a level signal 365 ($v$). The level signal 365 is applied to the TNR module 372 and the secondary gain application module 374. The audio signal 351 is also applied to the impulse detector 366. The impulse detector 366 is configured to analyze the audio signals 351 for the presence (or absence) of impulse (transient) sounds and produces an output signal 367, sometimes referred to herein as an impulse level signal which indicates the size or other parameter measures of the impulse, or Boolean or logic signal (h) which indicates the presence (or absence) of impulse sounds in the audio signals. That is, in certain examples, the output signal 367 may be an impulse level measure, measuring the size, degree, or other parameters of the impulse (i.e., a gain to appropriately remove the impulse from the resultant signal 375. In other examples, as noted above with reference to FIG. 3B, the output signal 367 may be a Boolean signal that is True when an impulse sound is present, and False when no impulse sound is present.

In the embodiment of FIG. 3C, the Boolean signal 367 is applied to the TNR module 372. When the Boolean signal 367 indicates that an impulse sound is present, the TNR module 372 is configured to generate a TNR gain 373 that can be applied to the level signal 365 at the secondary gain application module 374. The TNR gain 373 is generally configured so as to attenuate (i.e., reduce, and/or eliminate) the impulse sound in the gain function input signal 375 that is provided to the impulse-unaware gain function 376. Stated differently, when the TNR gain 373 is applied to the level signal 365, the gain function input signal 375, which is generated by the secondary gain application module 374, is a signal in which the impulsive noises have been significantly attenuated.

Using the gain function input signal 375, the impulse-unaware gain function 376 generates a time-variable gain 369 ($g$) that is applied to the audio signal 351 at the gain application module 370. As noted above, the time-variable gain 369 operates to reduce (attenuate) the audio signal amplitude when the level signal 365 exceeds a threshold or kneepoint and, as such, application of the time-variable gain 369 to the audio signal 351 produces the compressed audio signal 353 ($y$).

As noted, in the embodiment of FIG. 3C the TNR module 372 generates a TNR gain 373 only when an impulse sound is present in the audio signal 351 and, as such, a TNR gain 373 is only applied to the level signal 365 when an impulse sound is present in the audio signal. Therefore, the gain function input signal 375 may correspond to the level signal 365 (i.e., when no impulse sound is present in the audio signal 351) or to an attenuated version of the level signal 365.

The impulse-unaware gain function 376 operates in a substantially consistent manner, regardless of whether the TNR gain 373 is applied to the level signal 365. That is, the impulse-unaware gain function 376 consistently operates to generate a time-variable gain based on the levels received at its input (i.e., the level indicated by the output signal 375). Since the gain function 376 operates in the substantially consistent manner, it is "unaware" of whether or not an impulse sound was present in the audio signal 351 (i.e., either it is not present or the impulse sound is actively removed by application of the TNR gain 373). However, because any impulse sounds are actively removed before the impulse-unaware gain function 376, the time-variable gain 369 generated by the impulse-unaware gain function 376 will not affect the impulse sound with the first processing path (i.e., in the original audio signal). Stated differently, the time-variable gain 369 is decoupled from (i.e., generally/substantially unrelated to) a level of the impulse sound and is decoupled from energy that is part of the impulse sound (i.e., substantially derived from energy that is not part of the impulse sound).

In certain embodiments, the impulse-unaware gain function 376 is an Automatic Gain Control (AGC) system that operates in accordance with one or more "attack times" and/or "release times" and can be triggered at an audio signal level, referred to as a "kneepoint." If the detected audio signal 351 has an amplitude (level) which crosses above the kneepoint (as indicated in the gain function input signal 375), then the impulse-unaware gain function 376 is activated to implement a reduction in the gain (i.e., the gain in dB is negative). The initial gain reduction typically occurs over a relatively short time period (the "attack time"). When the level reduces below the kneepoint, the gain gradually recovers back to its default value, typically over a longer time period (the "release time"). It is to be appreciated than a gain system in accordance with embodiments presented herein may also or alternatively include multiple stages that each having different associated kneepoints and release times.

In summary, FIG. 3C illustrates an embodiment in which, when impulse sounds are detected, the impulse sound is attenuated only in the signals that are provided to the impulse-unaware gain function 376. The TNR gain 373 is applied only for the purpose of calculation of the time-variable gain 369, but is not applied to the input signal 351 as heard by a recipient (i.e., within the first processing path). Since the impulse-unaware does not see the energy of the impulses, the gain function does not react to attenuate the impulses and the time-variable gain 369 is substantially derived from energy that is not part of the impulse sound. The effect is that the impulse sounds are left to pass through to the loudness growth function. In other words, the impulse-aware gain system 352(C) operates in an opposite manner to conventional arrangements in that the gain system deliberately does not suppress the impulse sound within the within the first processing path. Instead, the embodiment of FIG. 3C allows the impulse sounds to pass through to the subsequent LGF 360 (FIG. 3A) to prevent the impulse sound from being too loud. Because the LGF 360 acts instantaneously (i.e., it has zero attack and release times), there is no detrimental effect on speech that immediately follows the impulse sound.

Figure 5A:
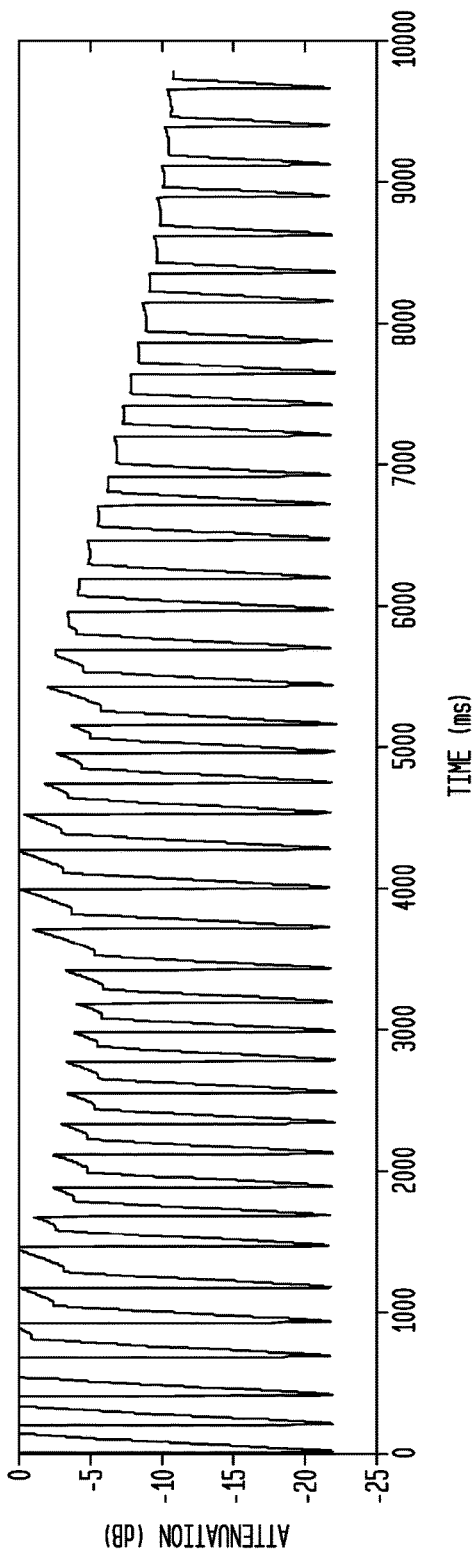
FIG. 5A is a graph illustrating operation of a conventional gain system in the presence of impulse sounds.
Figure 5B:
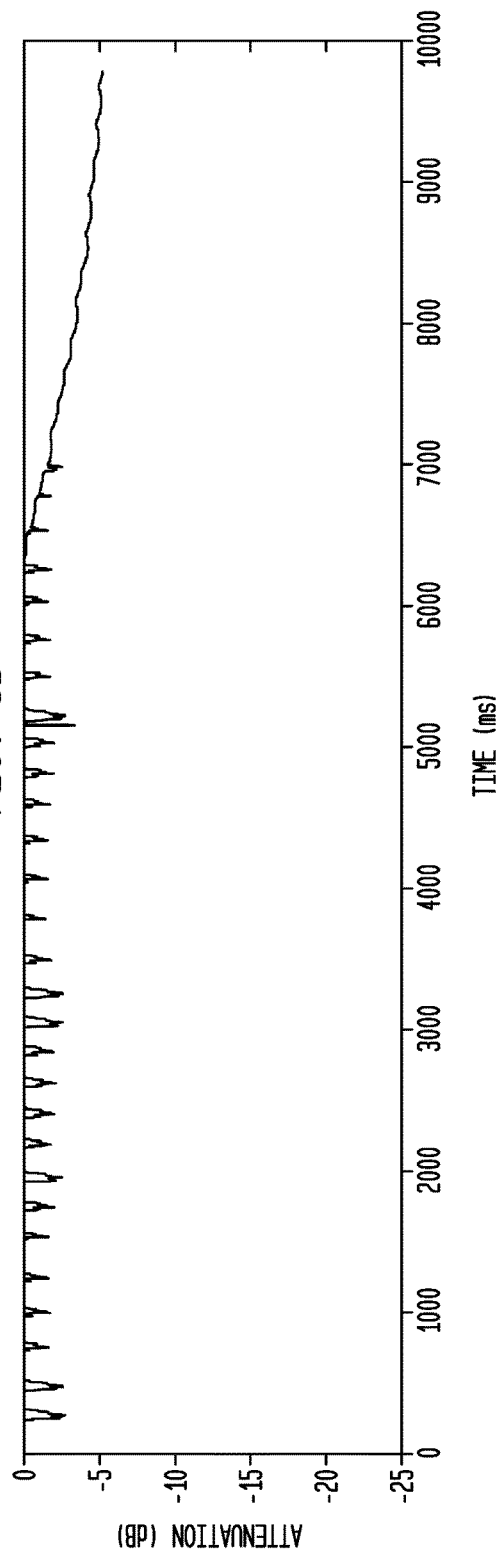
FIG. 5B is a graph illustrating operation of an impulse-aware gain system in the presence of impulse sounds, in accordance with certain embodiments presented herein.

FIG. 5A is a graph illustrating the attenuation provided in a conventional tri-loop gain system (i.e., an Automatic Gain Control (AGC) system with three AGC stages each having different associated kneepoints and release times), while FIG. 5B is a graph illustrating the attenuation provided in an impulse-aware gain system in accordance with embodiments presented herein. As shown in FIG. 5A, without the impulse awareness, the signals are attenuated by about 10 dB continuously, and up to 20 dB from the fast AGC stage (troughs). As shown in FIG. 5B, with the impulse-aware gain system, the signals are only minimally attenuated and only a constant 5 dB slow attenuation is applied. That is, FIG. 5B illustrates the intended effect in that the impulse sounds pass through the impulse-aware gain system with less attenuation, wherein the amount of attenuation is based on a level of the audio signal prior to detection of the impulse sound.

Figure 6A:
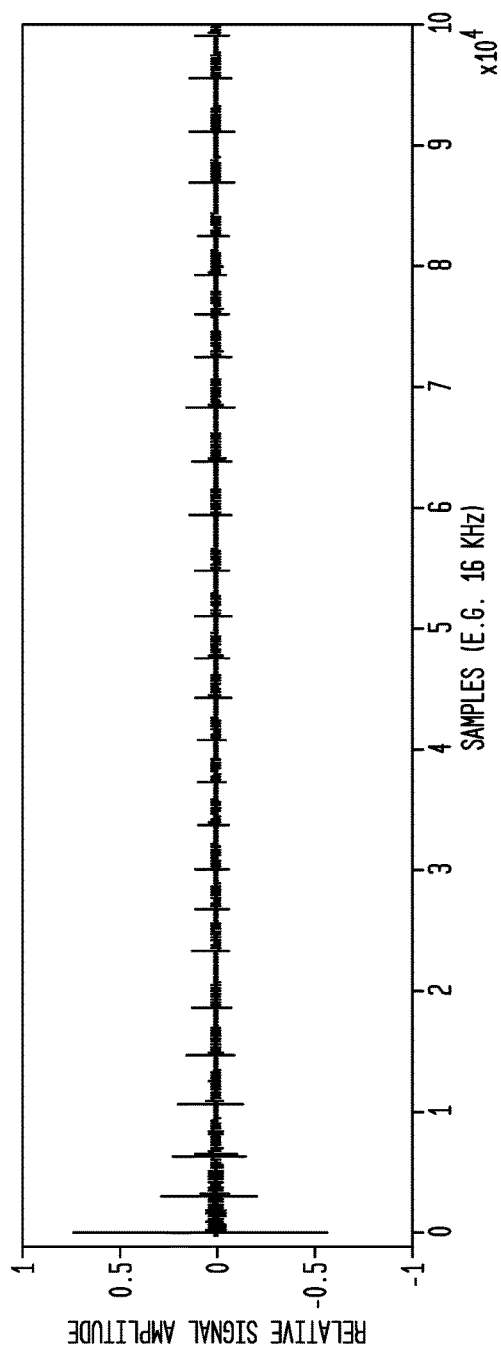
FIG. 6A is a graph illustrating operation of a conventional gain system in the presence of impulse sounds.
Figure 6B:
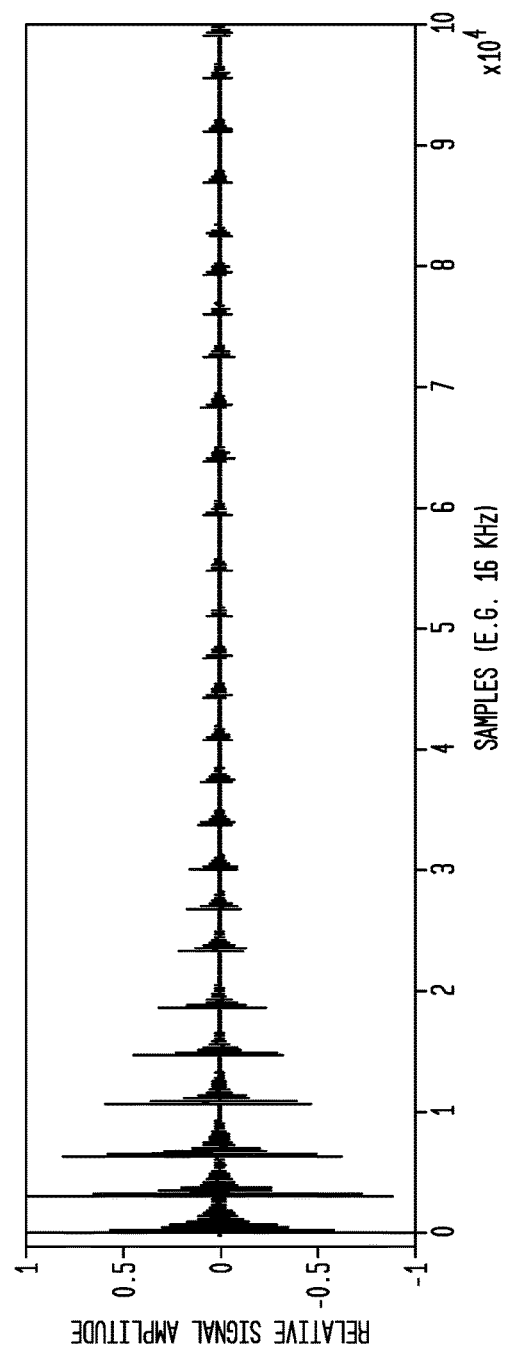
FIG. 6B is a graph illustrating operation of an impulse-aware gain system in the presence of impulse sounds, in accordance with certain embodiments presented herein.

FIG. 6A is another graph illustrating conventional gain system operation, while FIG. 6B illustrates the operations of an impulse-aware gain system. As shown in FIG. 6B, when an impulse sound is detected, the time-variable gain is held constant. In this way, the impulse remains as it is, such that there is minimal fast distortion to the output, and only minimal long term attenuation which would turn down the target signal.

Figure 7:
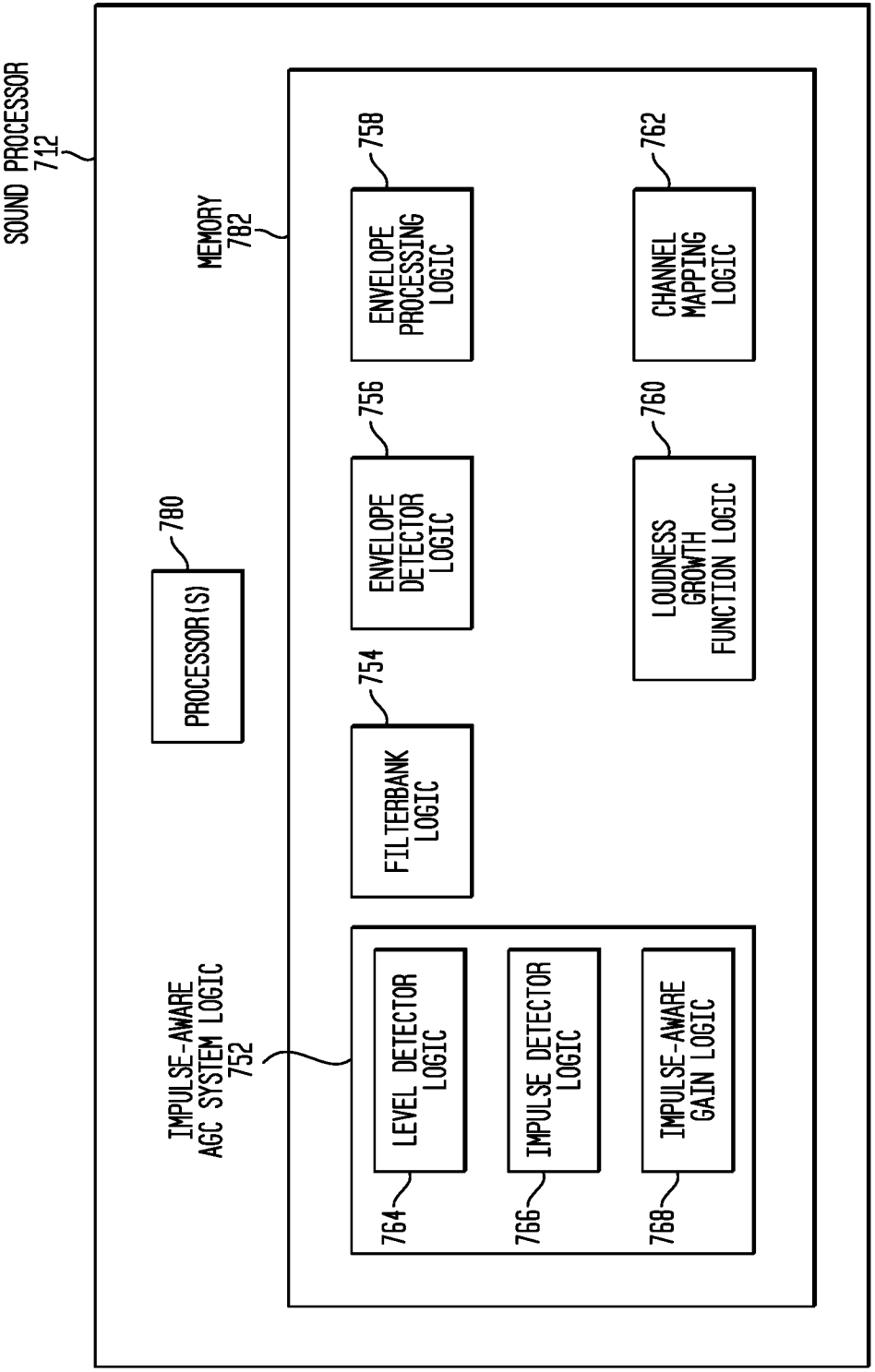
FIG. 7 is a block diagram of a sound processor, in accordance with certain embodiments presented herein.

FIG. 7 is a schematic block diagram illustrating an arrangement for a sound processor, referred to as sound processor 712, in accordance with an embodiment of the present invention. As shown, the sound processor 712 includes one or more processing elements/units 780, sometimes referred to as central processing units (CPUs) or simply processors, and a memory 782. The memory 782 includes a number of functional (logic) modules/units, including impulse-aware gain system logic 752, filterbank logic 754, envelope detector logic 756, envelope processing logic 758, loudness growth function logic 760, and channel mapping logic 762. The impulse-aware gain system logic 752 includes level detector logic 764, impulse detector logic 766, and impulse-aware gain logic 768.

The memory 782 may be read only memory (ROM), random access memory (RAM), or another type of physical/tangible memory storage device. Thus, in general, the memory 782 may comprise one or more tangible (non-transitory) computer readable storage media (e.g., a memory device) encoded with software comprising computer executable instructions and when the software (i.e., logic modules/units) is executed (by the one or more processors 780) it is operable to perform the operations described herein with reference to a sound processor, including the impulse-aware AGC operations described above.

FIG. 7 illustrates a software implementation for a sound processor. However, it is to be appreciated that one or more operations associated with a sound processor in accordance with embodiments presented herein may be partially or fully implemented with digital logic gates in one or more application-specific integrated circuits (ASICs).

Figure 8:
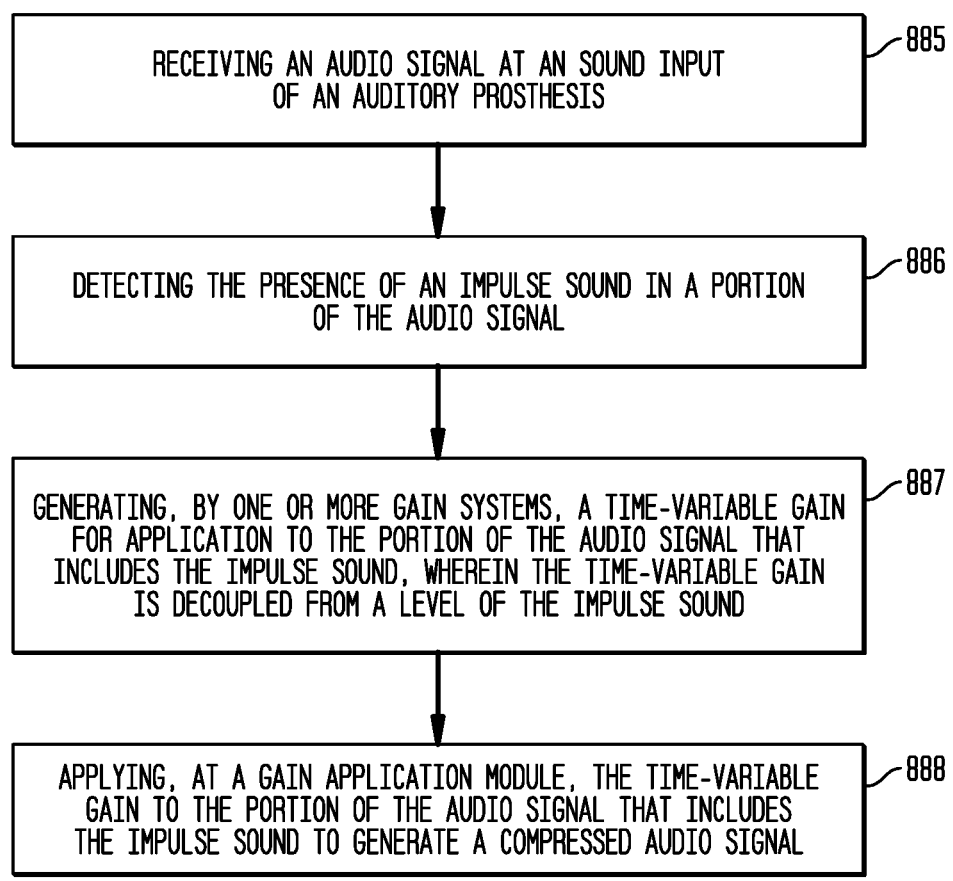
FIG. 8 is a flowchart of a method, in accordance with certain embodiments presented herein.

FIG. 8 is a flowchart of a method 884 in accordance with embodiments presented herein. Method 884 begins at 885 an audio signal is received at a sound input of an auditory prosthesis. At 886, the auditory prosthesis detects the presence of an impulse sound in a portion of the audio signal. At 887, one or more gain systems generate a time-variable gain for application to the portion of the audio signal that includes the impulse sound, where the time-variable gain is decoupled from a level of the impulse sound. At 888, a gain application module applies the time-variable gain to the portion of the audio signal that includes the impulse sound to generate a compressed audio signal.

As noted above, an impulse-aware gain system in accordance with embodiments presented herein includes an impulse detector that is configured to analyze/evaluate audio signals for the presence of impulse (transient) sounds. As noted, impulse sound are sounds that have a short overall duration (e.g., a duration on the order of a few milliseconds), are relatively loud (e.g., a level/amplitude that is well above the long-term sound average), and have a fast decay time (e.g., a decay time on the order of tens of milliseconds). In one example, the decay time is the time that it takes the impulse to decay from its peak to 10 or 20 dB below its peak. Impulse sounds can originate from a large number of sources and may include, for example, firearm discharges, dishes clinking together, typing on a computer, keys rattling, doors slamming, chairs moving, hammering, etc. In many of these examples, the peak sound pressure level (SPL) of the impulse sounds are over 100 dB, and up to 180 dB.

The detection of impulse sounds, sometimes referred to herein as "impulse detection," may be implemented in a number of different manners. As noted above, sound processors may include a filterbank (e.g., FFT) and the impulse-aware gain systems are generally shown and described as proceeding the filterbank. However, it is to be appreciated that this is illustrative and that the impulse detection could be performed using the filtered signals (i.e., the signals after the FFT) or the unfiltered signals (i.e., the signals before the FFT). That is, the impulse detection can make use of (1) the broadband signals that exist prior to the FFT or (2) the post-FFT band limited signals, which are taken from the broadband signals with the addition of a short delay filter (such as a high pass filter). In one specific example, a frequency domain Root Mean Square (RMS) calculation is performed after the FFT to obtain only a selected band-limited signal (e.g., only the mid or high frequency ranges). In summary, depending on different factors, it can be advantageous to use different signals (i.e., signals in different processing stages) for the impulse detection. For example, it may be advantageous to use a signal with less delay in it (such as caused by FFT processing) since impulses occur very quickly and any internal delay in detecting the impulses can mean the attenuation, or Boolean detection, misses the very start of the impulse. In certain examples, it may be beneficial to exclude low frequency signals when detecting impulses since some impulsive-like signals in the low frequency range which high amplitudes which cause false positives.

One illustrative impulse detection technique incorporates a signal smoothing operation and performs one or more comparisons between a smoothed input signal and the original (raw) input signal. More specifically, FIG. 9A is a block diagram of an impulse detector, referred to as impulse detector 966(A), in accordance with certain embodiments presented herein.

Figure 9A:
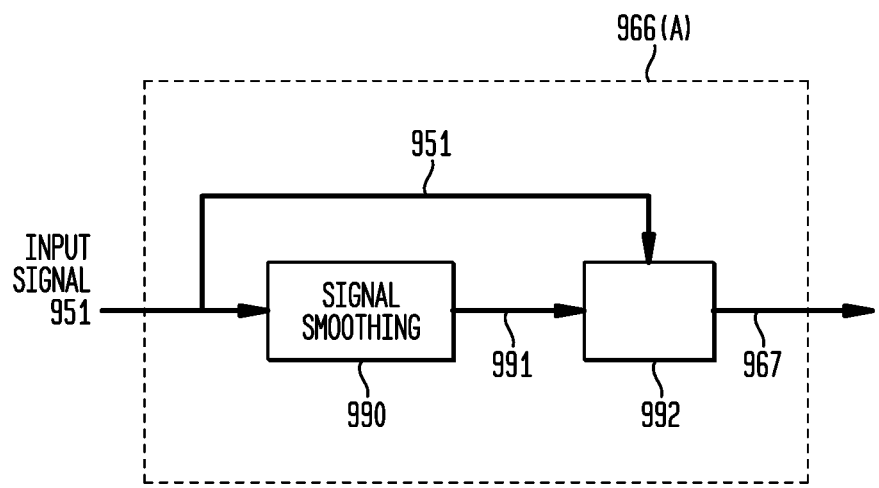
FIG. 9A is a block diagram of an impulse detector, in accordance with certain embodiments presented herein.

In the embodiment of FIG. 9A, the impulse detector 966(A) receives an input (audio) signal 951. The impulse detector 966(A) includes a signal smoothing module 990 that is configured to smooth the input signal 951 in accordance with a time constant (i.e., over a preceding time period). The signal smoothing module 990 may make use of different time constants (time periods), such as 2 ms, 10 ms, 20 ms, etc. The signal smoothing module 990 generates a smoothed input signal 991 that is provided to a comparison module 992. The comparison module 992 calculates a difference between the smoothed input signal 991 (indicating a longer time estimate of the input signal) and the input signal 951 itself.

The comparison module 992 also determines whether the difference exceeds a predetermined threshold (e.g., the smoothed signal is subtracted from the input signal itself to generate determine an instantaneous signal relative to a short term mean of the signal). In one example, this is implemented through a first order IIR filter on the dB input signal. When the smoothed signal (short time estimate) is subtracted from the input signal, a short term deviation measure is created.

In one example, the comparison module 992 generates a output 967 which is an impulse level measure signal or a Boolean output that has a state (i.e., an impulse level measure like the impulse level in dB above the non-impulsive background noise, or True (1) or False (0)) that depends on whether the difference between the smoothed input signal 991 and the input signal 951 exceeds a predetermined threshold. In general, for speech signals, the differences from the short term mean are low due to speech characteristics. Due to their very fast rise times, impulse sounds have large differences from the short term mean.

In certain embodiments, the an impulse-aware gain system in accordance with embodiments presented herein may use a signal level detector in conjunction with the difference from the short term mean, to determine whether an impulse is present. For example, FIG. 9B is a block diagram of an impulse detector, referred to as impulse detector 966(A), in accordance with certain embodiments presented herein.

Figure 9B:
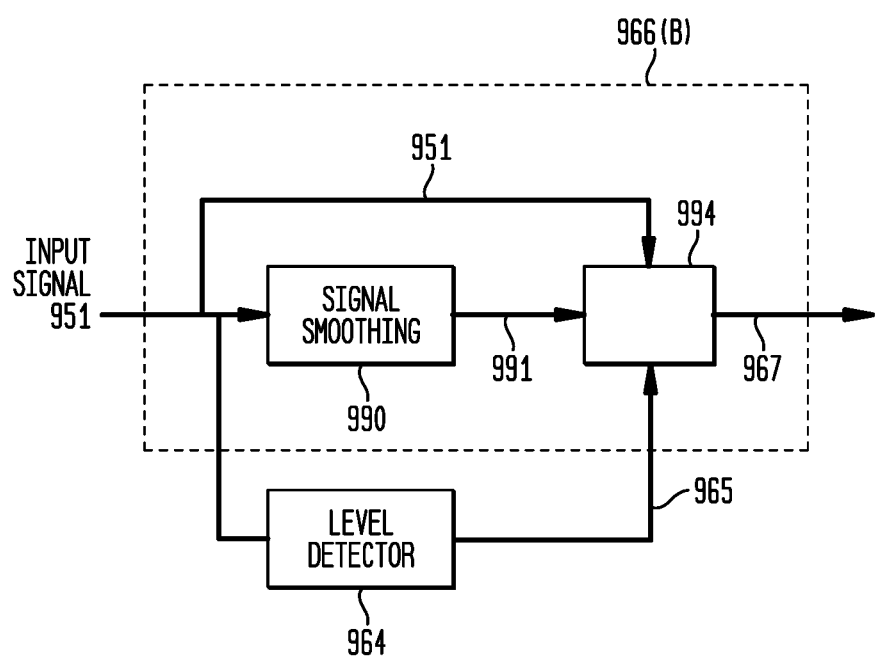
FIG. 9B is a block diagram of an impulse detector, in accordance with certain embodiments presented herein.

In the embodiment of FIG. 9B, the impulse detector 966(B) receives an input (audio) signal 951. The impulse detector 966(B) includes a signal smoothing module 990 that is, as described above with reference to FIG. 9A, is configured to smooth the input signal 951 in accordance with a time constant. The signal smoothing module 990 generates a smoothed input signal 991 that is provided to a comparison module 994. The comparison module 994 is similar to comparison module 992 of FIG. 9A in that the comparison module 994 also calculates a difference between the smoothed input signal 991 (indicating a longer time estimate of the input signal) and the input signal 951 itself. The comparison module 994 also determines whether the difference exceeds a predetermined threshold (e.g., the smoothed signal is subtracted from the input signal itself to generate determine an instantaneous signal relative to a short term mean of the signal. When the smoothed signal (short time estimate) is subtracted from the input signal, a short term deviation measure is created.

Similar to FIG. 9A, the comparison module 994 generates an output 967, which is an impulse level measure signal or a Boolean output that has a state (i.e., an impulse level measure like the impulse level in dB above the non-impulsive background noise, or True (1) or False (0)) that depends on whether the difference between the smoothed input signal 991 and the input signal 951 exceeds a predetermined threshold. However, in FIG. 9B, the comparison module 994 also receives a level signal 965 from a level detector 964. The level signal 965 is used as used as a secondary control of the output 967. More specifically, the comparison module 994 is configured to determine the level of the input signal 951, as indicated by level signal 965, prior to generating the output 967 and/or prior to performing the comparison. When the level of the input signal 951 is below a predetermined level threshold (e.g., 60 dB, 70 dB, etc.), the output 967 may have a False state, regardless of the results of the difference comparison. The predetermined level threshold is selected so that impulse sounds of sufficiently low amplitude (e.g., typing on a keyboard) that may not be detrimental due to their low peak amplitude, do not trigger the impulse sound related operations described above. By using both the difference from the short term mean as well as information of the signal level/amplitude, the embodiment of FIG. 9A can detect and attenuate impulses more accurately.

The above embodiments have primarily been described with reference to the use of a single impulse detector. In certain examples, two or more impulse detectors may be provided and operate in parallel. For instance, there may be two impulse detectors that operate differently from one another. The differences in operation may include, for example, use of different short term smoothing time constants to determine the difference from the short term mean signal, different level detector settings to determine an impulse (e.g., as in FIG. 9B), different release times of the amplitude (or disable hold time for the Boolean system), or a combination of these or other parameter settings. The information from all of the parallel impulse detectors may be utilized to provide a more accurate determination of whether an impulse sound is present. In one embodiment, the information from all of the parallel impulse detectors may be combined (e.g., averaged). In another embodiment, an impulse is deemed to be detected if any of the parallel impulse detectors detects an impulse sound. In another example, an impulse is deemed to be detected only when all parallel impulses detectors detect an impulse. Similarly in an implementation such as that shown in FIG. 3C, information from both impulse detectors can be used to determine the TNR gains. In another example, the maximum attenuation (or minimum attenuation, or average attenuation) may be taken as the output gain from the parallel impulse detection implementation.

As described in detail above, embodiments of the present invention are generally directed to techniques for suppressing impulse/transient sounds in an auditory prosthesis. The techniques presented herein may be particularly advantageous in preventing impulse sounds from lowering the level of other sounds, and/or in the context of implantable microphones.

It is to be appreciated that the above described embodiments are not mutually exclusive and that the various embodiments can be combined in various manners and arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
   receiving an audio signal at a sound input of an auditory prosthesis;
   detecting the presence of an impulse sound in a portion of the audio signal;
   generating, by one or more gain systems, a time-variable gain for application to the portion of the audio signal that includes the impulse sound, wherein the time-variable gain is decoupled from a level of the impulse sound; and
   applying, at a gain application module, the time-variable gain to the portion of the audio signal that includes the impulse sound to generate a compressed audio signal.

2. The method of claim 1, wherein generating the time-variable gain for application to the portion of the audio signal that includes the impulse sound comprises:
   generating the time-variable gain based on a level of the audio signal prior to detection of the impulse sound.

3. The method of claim 2, further comprising:
   holding the time-variable gain at a constant level for a duration of the impulse sound so that the impulse sound passes through to a loudness growth function (LGF) with only application of a gain that is based on the level of the audio signal prior to the detection of the impulse sound.

4. The method of claim 1, wherein generating the time-variable gain for application to the portion of the audio signal that includes the impulse sound comprises:
   forwarding the audio signal along both a first and a second processing path, where the first processing path includes the gain application module and the second processing includes at least one gain function;
   without affecting the audio signal in the first processing path, actively attenuating the impulse sound in the audio signal within the second processing path before the audio signal reaches the at least one gain function.

5. The method of claim 1, further comprising:
   generating a plurality of channel signals from the compressed audio signal;
   generating envelope signals from the channel signals;
   applying a loudness growth function (LGF) to the envelope signals to produce channel magnitude signals, wherein a level of an impulse sound in a channel signal is reduced to a magnitude level that corresponds to a saturation level of the LGF.

6. The method of claim 1, wherein detecting the presence of an impulse sound in the audio signal comprises:
   generating, with a signal smoothing module, a smoothed sample of the audio signal over a period of time;
   determining, with a comparison module, a difference between the smoothed sample of the audio signal over the period of time and the audio signal; and
   determining, at the comparison module, whether the difference exceeds a predetermined threshold,
   wherein an impulse sound is detected only when the difference exceeds the predetermined threshold.

7. The method of claim 6, further comprising:
   receiving, at the comparison module, a level signal representing a level of the audio signal; and
   determining, at the comparison module, whether level of the audio signal exceeds a predetermined level threshold,
   wherein an impulse sound is detected when the difference and the level of the audio signal jointly exceed the predetermined difference and level thresholds.

8. The method of claim claim 3, wherein holding the time-variable gain at a constant level for a duration of the impulse sound comprises:
   temporarily suspending one or more operations of the one or more gain systems for the duration of the impulse sound.

9. An auditory prosthesis, comprising:
   one or more sound input elements configured to receive an audio signal; and
   a sound processor configured to convert the audio signal into one or more output signals for use in delivering electrical stimulation to a recipient,
   wherein the sound processor comprises at least one impulse-aware gain system configured to detect an impulse sound within the audio signal and to apply a time-variable gain to the audio signal, where the time-variable gain is decoupled from energy forming part of the impulse sound.

10. The auditory prosthesis of claim 9, wherein the at least one impulse-aware gain system is configured to generate the time-variable gain based on a level of the audio signal prior to detection of the impulse sound.

11. The auditory prosthesis of claim 10, wherein the at least one impulse-aware gain system comprises a level detector configured to determine a level of the audio signal, an impulse detector configured to detect the presence of the impulse sound in the audio signal, and an impulse-aware gain function configured to generate a constant gain that is applied to audio signal for the duration of the impulse sound.

12. The auditory prosthesis of claim 11, wherein the impulse-aware gain function is configured to operate in first and second modes of operation, wherein in the first mode of operation the impulse-aware gain function generates a time-variable gain for application to the audio signal and in the second mode of operation the impulse-aware gain function generates the constant gain that is applied to audio signal for the duration of the impulse sound, and wherein the second mode is activated in response to detection of the impulse sound.

13. The auditory prosthesis of claim 9, wherein the at least one impulse-aware gain system is configured to forward the audio signal along both a first and a second processing path, where the first processing path includes a gain application module configured to apply the time-variable gain to the audio signal and the second processing includes an impulse-unaware gain function, and wherein the at least one impulse-aware gain system is configured to attenuate the impulse sound in the audio signal within the second processing path before the audio signal reaches the impulse-unaware gain function.

14. The auditory prosthesis of claim 13, wherein the second processing path includes:
 a transient noise reduction module configured to generate a transient noise reduction gain configured to attenuate the impulse sound; and
 a secondary gain application module configured to apply the transient noise reduction gain to the audio signal in the second processing path before the audio signal reaches the impulse-unaware gain function.

15. The auditory prosthesis of claim 9, wherein the at least one impulse-aware gain system converts the audio signal into a compressed audio signal and wherein the sound processor further comprises:
 a filterbank configured to generate a plurality of channel signals from the compressed audio signal;
 an envelope detector configured to generate envelope signals from the channel signals; and
 a loudness growth function (LGF) configured to produce channel magnitude signals from the envelope signals, wherein a level of an impulse sound in a channel signal is reduced to a magnitude level that corresponds to a saturation level of the LGF.

16. The auditory prosthesis of claim 9, wherein the at least one impulse-aware gain system comprises at least one impulse detector comprising:
 a signal smoothing module configured to generate a smoothed sample of the audio signal over a period of time; and
 a comparison module configured to determine a difference between the smoothed sample of the audio signal over the period of time and the audio signal and to determine whether the difference exceeds a predetermined threshold,
 wherein an impulse sound is detected only when the difference exceeds the predetermined threshold.

17. The auditory prosthesis of claim 16, wherein the comparison module is further configured to receive a level signal representing a level of the audio signal and to determine whether level of the audio signal exceeds a predetermined level threshold,
 wherein an impulse sound is detected when the difference and the level of the audio signal jointly exceed the predetermined difference and level thresholds.

18. The auditory prosthesis of claim 9, wherein the at least one impulse-aware gain system comprises a plurality of parallel impulse detectors each configured to operate differently, and wherein the least one impulse-aware gain system is configured to use outputs from each of the parallel impulse detectors to determine whether an impulse sound is present in the audio signal.

19. The auditory prosthesis of claim 9, wherein the auditory prosthesis is a cochlear implant.

20. An auditory prosthesis, comprising:
 at least one sound input element configured to receive an audio signal, and
 at least one gain system configured to:
  generate a time-variable attenuation for application to the audio signal, wherein the time-variable attenuation has a first value that is based on a level of the audio signal;
  detect an impulse sound in the audio signal, and
  hold the time-variable attenuation at the first value for a duration of the impulse sound regardless of a level of the impulse sound.

21. The auditory prosthesis of claim 20, wherein the at least one gain system comprises a level detector configured to determine the level of the audio signal, an impulse detector configured to detect the presence of the impulse sound in the audio signal, and an impulse-aware gain function configured to generate the time-variable attenuation.

22. The auditory prosthesis of claim 20, wherein the gain system is configured to forward the audio signal along both a first and a second processing path, where the first processing path includes a gain application module configured to apply the time-variable attenuation to the audio signal and the second processing includes an impulse-unaware gain function, and wherein the at least one gain system is configured to attenuate the impulse sound in the audio signal within the second processing path before the audio signal reaches the at impulse-unaware gain function.

23. The auditory prosthesis of claim 22, wherein the second processing path includes:
 a transient noise reduction module configured to generate a transient noise reduction gain configured to attenuate the impulse sound; and
 a secondary gain application module configured to apply the transient noise reduction gain to the audio signal in the second processing path before the audio signal reaches the impulse-unaware gain function.

24. The auditory prosthesis of claim 20, wherein the at least one gain system comprises a plurality of parallel impulse detectors each configured to operate differently, and wherein the least gain system is configured to use outputs from each of the parallel impulse detectors to determine whether an impulse sound is present in the audio signal.

* * * * *

UNITED STATES PATENT AND TRADEMARK OFFICE
CERTIFICATE OF CORRECTION

PATENT NO. : 10,492,007 B2
APPLICATION NO. : 15/628747
DATED : November 26, 2019
INVENTOR(S) : Brett Anthony Swanson et al.

Page 1 of 1

It is certified that error appears in the above-identified patent and that said Letters Patent is hereby corrected as shown below:

In the Claims

In Column 16, Line 10, after "processing" insert --path--

In Column 16, Line 10, after "function;" insert --and--

In Column 16, Line 17, after "signals" insert --and--

In Column 16, Line 44, delete "claim" (second occurrence)

In Column 17, Line 14, after "mode" insert --of operation--

In Column 17, Line 21, after "processing" insert --path--

In Column 18, Line 12, after "the" insert --at--

In Column 18, Line 42, after "processing" insert --path--

In Column 18, Line 46, delete "at"

In Column 18, Line 59, after "the" insert --at--

In Column 18, Line 59, after "least" insert --one--

Signed and Sealed this
Seventh Day of January, 2020

Andrei Iancu
*Director of the United States Patent and Trademark Office*